United States Patent [19]

Chou et al.

[11] Patent Number: 5,328,635

[45] Date of Patent: * Jul. 12, 1994

[54] IMINOALCOHOL-OXAZOLIDINE MIXTURES AND THEIR USE

[75] Inventors: Chih-Yueh Chou, Elk Grove; Pattabhi K. Raman, Downers Grove; Robert E. Malocha, Barrington; Thomas L. Johnson, Des Plaines; Vincent Nocito, Buffalo Grove; Marina D. Hoffman, South Holland; Patrick E. Brutto, Norridge, all of Ill.

[73] Assignee: ANGUS Chemical Company, Buffalo Grove, Ill.

[*] Notice: The portion of the term of this patent subsequent to Jun. 29, 2010 has been disclaimed.

[21] Appl. No.: 866,662

[22] Filed: Apr. 8, 1992

Related U.S. Application Data

[63] Continuation-in-part of Ser. No. 624,062, Dec. 4, 1990, Pat. No. 5,264,148, and a continuation-in-part of Ser. No. 745,476, Aug. 15, 1991, Pat. No. 5,223,174.

[51] Int. Cl.$^5$ ............... C09K 3/00; B01D 19/04
[52] U.S. Cl. .................. 252/194; 252/321; 252/392; 252/394; 106/14.05
[58] Field of Search ............ 252/194, 392, 394, 321, 252/315.1, 70, 311

[56] References Cited

U.S. PATENT DOCUMENTS

| | | | |
|---|---|---|---|
| 2,737,491 | 3/1956 | Hughes | 252/8.55 |
| 2,924,571 | 2/1960 | Hughes | 252/8.55 |
| 4,094,812 | 6/1978 | Heyden et al. | 252/321 |
| 4,316,875 | 2/1982 | Barth | 422/133 |
| 4,443,577 | 4/1984 | Higgins | 524/590 |
| 4,582,543 | 4/1986 | Bretz | 148/6.15 R |
| 4,629,753 | 12/1986 | Quinn | 524/394 |
| 4,770,803 | 9/1988 | Forsberg | 252/75 |
| 5,126,421 | 6/1992 | Majewski et al. | 528/44 |
| 5,178,786 | 1/1993 | Jahnke et al. | 252/77 |
| 5,223,174 | 6/1993 | Chou et al. | 252/194 |

FOREIGN PATENT DOCUMENTS

| | | | |
|---|---|---|---|
| 3019356 | 11/1981 | Fed. Rep. of Germany . | |
| 172222 | 3/1976 | New Zealand | 9/666 |
| 179998 | 12/1977 | New Zealand | 9/666 |
| 194503 | 3/1983 | New Zealand | 9/669 |

Primary Examiner—Richard D. Lovering
Assistant Examiner—Joseph D. Anthony
Attorney, Agent, or Firm—Arnold, White & Durkee

[57] ABSTRACT

Methods of using a mixture as a corrosion inhibitor, moisture or formaldehyde scavenger, reactive diluent, rheological modifier, thermoplastic foam inhibitor, antifreezing agent, decolorizing agent, or drying agent. The mixture consists of from 0 to 100 mole percent of an iminoalcohol compound:

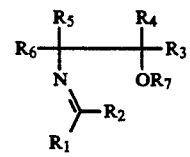

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of an oxazolidine compound having the structure:

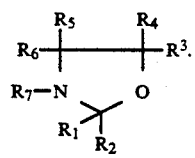

17 Claims, 3 Drawing Sheets

IMINOALCOHOL-OXAZOLIDINE MIXTURES AND THEIR USE

This application is a continuation-in-part of copending patent application Ser. No. 07/624,062 filed Dec. 4, 1990 now U.S. Pat. No. 5,264,148and application Ser. No. 07/745,476, filed Aug. 15, 1991 now U.S. Pat. No. 5,223,174.

BACKGROUND OF THE INVENTION

1. Field Of The Invention

The present invention is generally related to methods of using iminoalcoholoxazolidine mixtures. In particular, the present invention relates to methods of using the mixtures as a corrosion inhibitor, moisture or formaldehyde scavenger, reactive diluent, rheological modifier, thermoplastic foam inhibitor, antifreezing agent, decolorizing agent, or drying agent.

2. Background Of The Art

Moisture curable polyurethane coatings are extensively used as commercial and industrial protective and/or decorative coatings. Polyurethane coatings, known in the industry as one of the toughest coatings available, are routinely applied as protective coatings on exterior walls of buildings, industrial machinery, military equipment and vehicles, commercial and passenger vehicles, and any other surface requiring a protective coating. Moisture curable polyurethane systems are also used extensively as sealants and adhesives.

Moisture curing polyurethane coating systems include a polyisocyanate component which reacts with atmospheric water at room temperature to form useful films. These systems also include pigments, organic solvents, and a variety of adjuvant components, e.g., surface active agents, dispersants, diluents, and filters. Since the polyisocyanate component reacts with even trace amounts of moisture, extreme care must be taken so that the polyisocyanates do not contact water until they are applied to a surface to be coated. Water is, however, unintentionally and unavoidably introduced into the formulation process in the form of dissolved water in solvents, adsorbed and absorbed moisture on the surfaces of fillers and pigments, and atmospheric moisture. Subsequent reaction of the water with the polyisocyanate component of the system results in an irreversible reaction which will harden the product, making it unusable before it can be applied to the surface to be coated. This water must be removed in order to produce an acceptable product. The existing methods for preparing color-pigmented moisture curable polyurethane coatings require expensive equipment to dry the pigments, solvents, and fillers. In the alternative, moisture scavenging agents are added to the coating preparation or are added to the pigments, solvents and other raw materials prior to preparing the coating.

One group of moisture scavenging compounds are the molecular sieves. Molecular sieves adsorb water into their pores, thereby binding the water and preventing it from reacting with the polyisocyanate component. An example of a molecular sieve is sodium potassium aluminosilicate, available from the Mobay Corp., Pittsburgh, Pa., under the tradename designation Baylith L Powder. One disadvantage of using molecular sieves is that they reduce the gloss of the cured coating. Another disadvantage of molecular sieves is that they will sometimes plasticize or embrittle the cured coating.

A second group of water scavenging agents widely used to prevent moisture contamination of moisture curable polyurethane coating systems is the monomeric isocyanates. A typical monomeric isocyanate, such as p-toluenesulfonyl isocyanate (Vanchem, Inc. Lockport, Conn.), reacts with water to generate carbon dioxide and the corresponding sulfonamide, e.g., p-toluenesulfonamide. The carbon dioxide diffuses from the pigment grind during the dehydration phase as carbon dioxide gas. A disadvantage of monomeric isocyanates is that they are harmful if swallowed, inhaled, or absorbed through the skin and are extremely corrosive to the tissues of the mucous membranes, upper respiratory tract, and skin.

There is a need for a moisture scavenger which efficiently, cost effectively, and safely removes water from moisture curable coating systems and from any other preparation where residual water is a problem, without seriously detracting from the performance of the cured coating.

Coating, adhesive or sealant formulations also may include rheological modifiers to reduce viscosity, disperse pigments and improve solvency and flow. Formulations which do not contain rheological modifiers may exhibit a rapid increase in viscosity for a relatively small increase in solids content. The increased viscosity causes the formulation to set quickly resulting in striations in the formulation. Addition of a rheological modifier enables the formulation to flow into a smooth layer before it sets. Conventional rheological modifiers include polyethylene glycols such as Carbowax and polyethylene oxides such as Polyox.

There is a need for a rheological modifier to reduce viscosity and volatile organic content, disperse pigments, and improve the solvency and flow properties of a coating, adhesive or sealant.

Radiation curable coatings are generally composed mainly of radiation curable multifunctional monomers, oligomers and polymers. Restrictions on solvent content in the atmosphere have increased efforts to provide radiation curable coatings which do not contain any volatile components, but instead include components which form either the whole or a part of the hardened film itself. Reactive diluents are used to lower the volatile content of the coatings by reducing the loss of organic solvents into the atmosphere. Reactive diluents are compounds of low volatility which reduce the viscosity of a coating, adhesive or sealant formulation and become a permanent part of the formulation through chemical reaction. Accordingly, reactive diluents are added to radiation curable coatings not only as a diluent, but to reduce viscosity, copolymerize with the oligomers and polymers to form a part of the coating, and contribute to the final properties of the cured film. Examples of reactive diluents for use in coatings are monofunctional acrylic monomers, multifunctional acrylates and methacrylates of alkoxylated and non-alkoxylated polyols such as trimethylolpropane triacrylate, trimethylolpropane trimethacrylate, pentaerythritol triacrylate and 1,6-hexanediol diacrylate and dimethacrylate, difunctional diluents such as 1,6-hexanediol diacrylate and dimethacrylate, and trifunctional diluents such as trimethylolpropane triacrylate and pentaerythritol triacrylate. These reactive diluents pose problems which limit their use in radiation curable coatings. The diluents are known to produce brittle films with severe shrinkage and poor adhesion to substrates, exhibit slow cure response or poor solvency effects, ineffectively reduce viscosity, or cause serious skin irritancy problems.

There is a need for a reactive diluent which exhibits good cure response, low intrinsic viscosity, low film shrinkage, and excellent solvating or viscosity reducing properties.

Formaldehyde is a raw material frequently used in polymeric systems including phenol-formaldehyde, urea-formaldehyde, and melamine-formaldehyde. Exposure to formaldehyde vapors in the workplace is stringently controlled by the use of formaldehyde scavengers. Formaldehyde scavengers capture formaldehyde and hold it in a form having significantly lower formaldehyde vapor pressure. Products such as textiles and plywood typically contain a formaldehyde scavenger to reduce free formaldehyde levels without changing the physical properties of the products. Known formaldehyde scavengers include nitroparaffins such as nitromethane (NM TM), nitroethane (NE TM), 1-nitropropane (NiPar S-10 TM) and 2-nitropropane (NiPar S-20 TM), and amino alcohols such as 2-amino-2-methyl-1-propanol (AMP TM), 2-amino-2-ethyl-1,3-propanediol (AEPD ®) and tris(hydroxymethyl)aminomethane (TRIS AMINO ®), which are manufactured by ANGUS Chemical Company.

There is a need for a formaldehyde scavenger which efficiently, cost effectively, and safely removes formaldehyde from polymeric systems and from any other preparation where free formaldehyde is a problem, without seriously detracting from the performance or physical properties of the system.

Corrosion is often prevalent in engine cooling systems. Metals such as copper, iron, steel, aluminum, magnesium and the like are often exposed to high temperatures, pressures and flow rates in these cooling systems. These conditions corrode metal forming corrosion products which may cause engine overheating or engine failure. Lightweight metals in engine components such as aluminum and magnesium are subject to pitting of radiator tubes, crevice corrosion at hose connections, and deposit corrosion from deposition of corrosion products. Corrosion inhibitors are added to antifreeze/coolant compositions and functional fluids which contact metal to prevent and control corrosion in engine cooling systems and other machinery. U.S. Pat. No. 4,282,108 describes oxazolidine derivatives which are used as chelants, anti-copper-corrosion additives and frictional modifiers in automatic transmission fluid, an oxidation inhibitors in middle distillate fuels.

There is a need for a corrosion inhibitor which effectively reduces the incidence of corrosion of metals or alloys, and which may be applied to a surface of a metal or alloy or may be incorporated in a functional fluid which contacts a surface of a metal or alloy.

Phenol-based peroxide inhibitors have been suggested as a substitute for 2,6-di-t-butyl-p-cresol for use in polyol formulations because of the limited supply of the conventional p-cresol inhibitor. However, the phenol-based inhibitors cause discoloration of the polyol. N-(2-hydroxyalkyl)oxazolidines are known decolorizing agents for removing color-forming bodies from a mixture of alkyl substituted phenols.

There is a continuing need for a decolorizing agent which removes the color from a phenol, amine or other discolored preparation.

SUMMARY OF THE INVENTION

The present invention provides a method of scavenging formaldehyde from a preparation by admixing with the preparation an effective amount of a mixture consisting of:

from 0 to 100 mole percent of the compound:

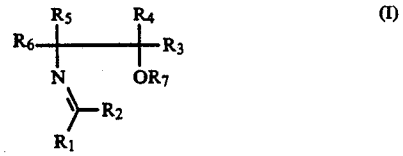

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of the compound:

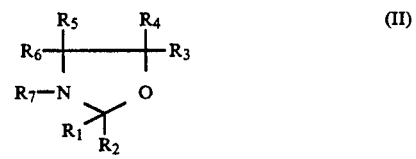

wherein: $R_1$, $R_2$, $R_3$, $R_4$, $R_5$, $R_6$ and $R_7$ are as defined above for compound (I). An effective amount of the mixture including at least one of the formaldehyde scavenging compounds (I) and (II) described above is intimately admixed with the preparation. In a preferred embodiment, the formaldehyde scavenging compound is at least one of a ketimine or aldimine alcohol of compound (I) and an oxazolidine compound (II) and the effective amount of the mixture includes from 1 to about 100 moles of the mixture for every mole of formaldehyde in the preparation.

A second aspect of the invention is directed to a method of scavenging moisture from a preparation. According to the method, an effective amount of the mixture including at least one of the moisture scavenging compounds (I) and (II) described above is intimately admixed with the preparation. In a preferred embodiment, the moisture scavenging compound is at least one of a ketimine or aldimine alcohol of compound (I) and an oxazolidine compound (II) and the effective amount of the mixture includes from 1 to 100 moles of the mixture for every mole of water in the preparation. The preparation is preferably a composite, sacrificial pigment, gas, ink, industrial fluid, coating, adhesive, sealant, or coating component.

A third aspect of the present invention is a method of inhibiting corrosion of a metal or alloy. An effective amount of the mixture including at least one of the corrosion inhibiting compounds (I) and (II) described above intimately contacts the metal or alloy. In a preferred embodiment, the metal or alloy is coated with the mixture. Alternatively, the mixture is admixed with an industrial fluid. Preferably, from 1 to about 100 moles of the mixture is added for every mole of water in the industrial fluid.

A fourth aspect of the present invention is a method of reducing volatile organic content and a concentration of an active material in a preparation and improving rheological properties of the preparation using a reactive diluent. An effective amount of the mixture including at least one of the reactive diluent compounds (I) and (II) described above is admixed with the preparation. Preferably, from 1 to about 50 wt. % of the mixture is added based on the total weight of the preparation.

Another aspect of the present invention is a method of modifying the rheology of a preparation. An effective amount of the mixture including at least one of the rheological modifier compounds (I) and (II) described above is admixed with the preparation. Preferably, from 1 to about 50 wt. % of the mixture is added based on the total weight of the preparation.

A further aspect of the invention is a method of reducing foaming of a thermoplastic. An effective amount of the mixture including at least one of the foam inhibiting compounds (I) and (II) described above is admixed with the thermoplastic. Preferably, from 1 to about 100 moles of the mixture is added for every mole of water in the thermoplastic.

Still another aspect of the invention is directed to a method for preventing the formation of ice crystals and for depressing the freezing point of a preparation. According to the method, an effective amount of the mixture including at least one of the antifreeze compounds (I) and (II) described above is intimately admixed with the preparation. The preparation is preferably an industrial fluid. In a preferred embodiment, the moisture scavenging compound is at least one of a ketimine or aldimine alcohol of compound (I) and an oxazolidine compound (II) and the effective amount of the mixture includes from 1 to 100 moles of the mixture for every mole of water in the preparation. If the preparation does not contain water, the effective amount of the mixture is from 1 to about 50 wt. % of the mixture based on the total weight of the preparation.

Another aspect of the present invention is a method of obtaining a stable dispersion, suspension or solution. An effective amount of the mixture including at least one of the stabilizing compounds (I) and (II) described above is admixed with the dispersion, suspension or solution. Preferably, from 1 to about 50 wt. % of the mixture is added based on the total weight of the dispersion, suspension or solution.

DETAILED DESCRIPTION OF THE INVENTION

Figure 1:
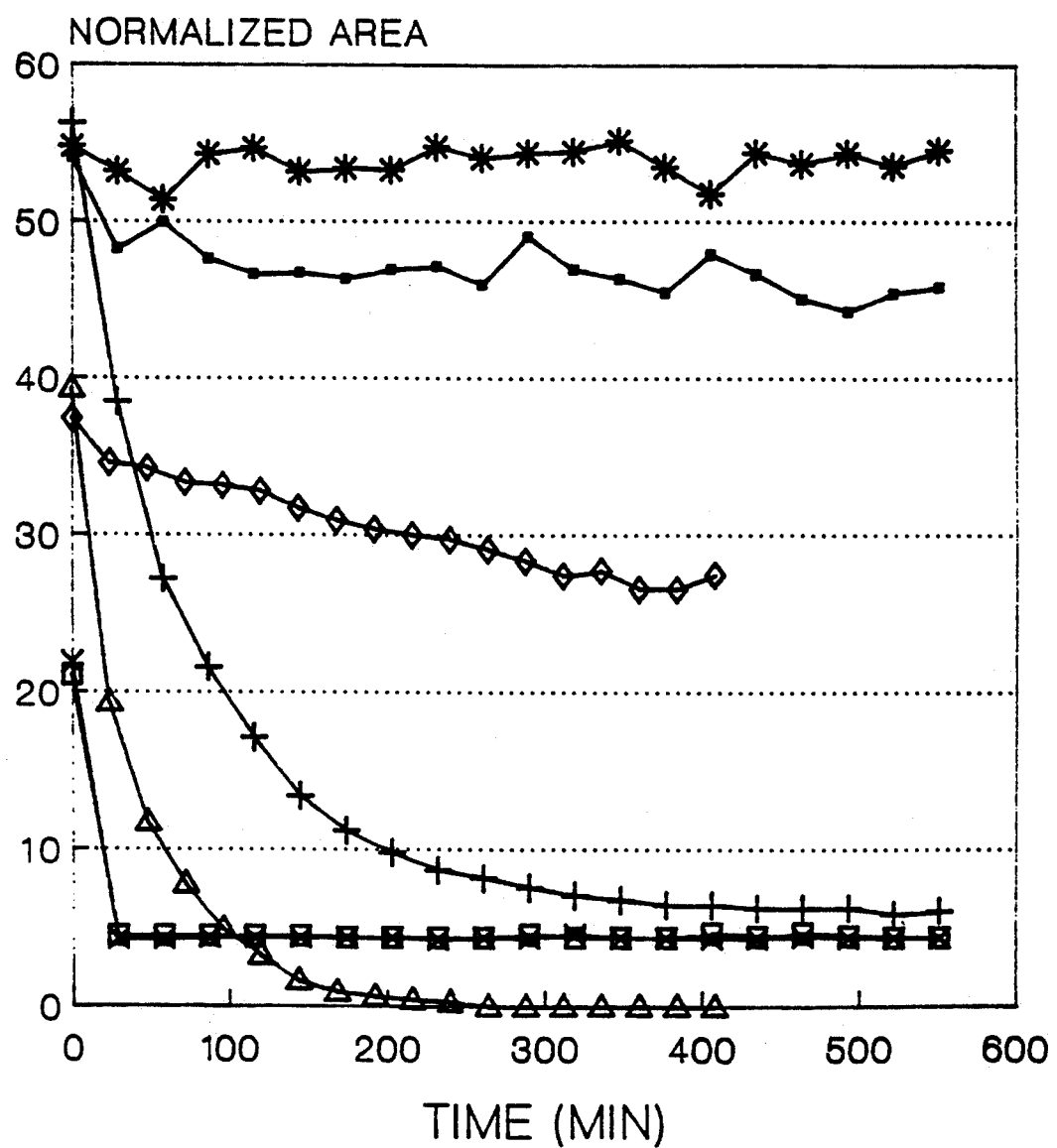
FIG. 1 graphically illustrates the relative hydrolysis rates of the 2-(1-hydroxy-2-hydroxymethylbutyl)(cyclohexylidine) amine/4-ethyl-4-hydroxymethyl-1,3-oxazolidine-2-spiro-1'-cyclohexane mixture (-··-), the 2-(1-hydroxybutyl)(1-phenyl-1-ethylidine) amine/4-ethyl-2-methyl-2-phenyl-1,3-oxazolidine mixture (-+-), the 2-(1-hydroxy-2-hydroxymethylbutyl)(1-phenyl-1-ethylidine) amine/4-ethyl-4-hydroxymethyl-2-methyl-2-phenyl-1,3-oxazolidine mixture (-*-), the 2-(1hydroxybutyl)(2-heptylidine) amine/4-ethyl-2-methyl-2-pentyl-1,3-oxazolidine mixture (-□-), the 2-(1-hydroxybutyl)(5-methyl-2-hexylidine) amine/4-ethyl-2-methyl-2-(3-methylbutyl)-1,3-oxazolidine mixture (-×-), the 2-(1-hydroxy-2-hydroxymethylbutyl)(5-methyl-2-hexylidine) amine/4-ethyl-4-hydroxymethyl-2-methyl-2-(3-methylbutyl)-1,3-oxazolidine mixture (-◇-), and the 2-(1-hydroxybutyl)(2,6-dimethyl-4-heptylidine) amine/2,2-(di-2-methylpropyl)-4-ethyl-1,3-oxazolidine mixture (-△-)

The present invention provides a mixture which can be advantageously used in the formulation of specialty polyurethane systems including sealants, adhesives and coatings. For the purposes of the present invention, a coating is any polyurethane coating, including both one and two component coatings. These coatings are typically cured by moisture, ambient, thermal, forced dry, radiation or bake curing. The mixture acts as a rheological modifier, drying agent, decolorizing agent, dispersant, and reactive diluent in these systems. Additionally, the mixture is a corrosion inhibitor, a reactive diluent in inks, a drying agent in inks, composites, sacrificial pigments, radiation cure coatings and industrial gasses, a foam inhibitor in thermoplastics, an antifreezing agent in functional fluids, and a formaldehyde scavenger in preparations such as polymeric systems, textiles and plywood.

It has been discovered that a class of compounds including ketimine and aldimine alcohols and substituted monocyclic oxazolidines are excellent moisture and formaldehyde scavengers, decolorizing agents, drying agents, corrosion inhibitors, reactive diluents, thermoplastic foam inhibitors, antifreezing agents, dispersants, and rheological modifiers. The prior art has disclosed a rather broad class of oxazolidine compounds as crosslinking reagents, reacting with polyfunctional isocyanates in the presence of polyols or water to form polymeric coatings. U.S. Pat. No. 4,101,527 discloses an equimolar reaction of an oxazolidine with a polyfunctional isocyanate in the presence of water to form a polyurethane coating. U.S. Pat. No. 3,941,753 describes pre-polymers for coating formation prepared from the reaction of a ketiminoalkanol with a polyisocyanate. Bicyclic moisture scavenging oxazolidine compounds for use in formulating polyurethane coatings are disclosed in copending U.S. patent application Ser. No. 07/624,062 by Chou, et al., entitled "Moisture Scavenging Oxazolidines", filed Dec. 4, 1990.

The mixture of the present invention consists of from 0 to 100 mole percent of an iminoalcohol compound:

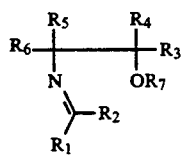

(I)

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of an oxazolidine compound:

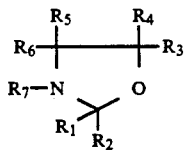

(II)

wherein: $R_1$, $R_2$, $R_3$, $R_4$, $R_5$, $R_6$ and $R_7$ are as defined above for compound (I).

Referring to the ketimine or aldimine alcohol compounds (I) of the present invention, the preferred R group substituents are those which increase the reactivity of the compound to water. Without limiting the invention, it has been discovered that amino containing $R_7$ substituents and aliphatic or aromatic R group substituents increase the reactivity of the compound to water. The moisture scavenging ketimine or aldimine alcohol compounds (I) of the present invention react chemically with water in the following manner:

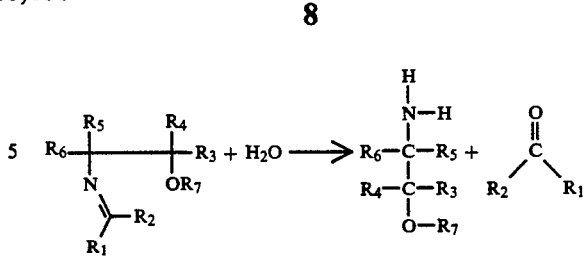

As shown above, the reaction products are an amino alcohol and a carbonyl compound. One mole of moisture scavenging ketimine or aldimine alcohol will react with and remove one mole of water. Therefore, it is preferred that the moisture scavenging mixtures of the invention containing ketimine or aldimine alcohols include at least one mole of the moisture scavenging ketimine or aldimine alcohol for each mole of water to be removed from a preparation. However, since a perfectly efficient reaction environment cannot be guaranteed in industrial settings, it is preferable that from 1 to about 10 moles of the moisture scavenging ketimine or aldimine alcohol be included for every mole of water to be removed from a preparation. Some applications require that only from 1 to about 3 moles of the moisture scavenging ketimine or aldimine alcohol be included for every mole of water to be removed from the preparation. Greater amounts of the ketimine or aldimine alcohol can be added to reduce the viscosity and/or volatile organic content of the preparation. As much as 100 moles of the mixture for every mole of water may be required to effect the desired change in the physical properties of the preparation.

All R group substituents which facilitate the reaction of water with the moisture scavenging ketiminoalkanol and aldiminoalkanol compounds (I) of the present invention are preferred. In one preferred embodiment of the invention, the $R_7$ substituent is a hydrogen atom, a methyl group, an ethyl group, a straight chain or branched chain alkyl group, an acyl group, an aryl group, an ester containing group, or an amino containing group; the $R_6$ substituent of the compound is a hydrogen atom or a methyl group; the $R_5$ substituent of the compound (I) is a hydrogen atom, a methyl or ethyl group, or a ($C_3$-$C_5$) branched chain or straight chain alkyl group; the $R_3$ and $R_4$ groups are, individually, hydrogen atoms or methyl groups; the $R_1$ substituent is an aryl group, an ethyl group or a ($C_3$-$C_5$) branched or straight chain alkyl group; and the $R_2$ substituent is a hydrogen atom, a methyl group, an ethyl group, or a ($C_3$-$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$-$C_5$) branched or straight chain alkyl group; the $R_2$ and $R_5$ substituents are methyl or ethyl groups, or ($C_3$-$C_5$) branched or straight chain alkyl groups; the $R_7$ substituent is a hydrogen atom, a methyl group, an ethyl group, an acyl group, an aryl group, an ester containing group, or an amino containing group; the $R_3$ and $R_4$ groups are, individually, hydrogen atoms or methyl groups; and the $R_6$ group is a hydrogen atom. Most preferably, the $R_1$ substituent is an aryl group or a ($C_3$-$C_5$) branched or straight chain alkyl group; the $R_2$ substituent is a methyl group, an ethyl group, or a ($C_3$-$C_5$) branched or straight chain alkyl group; the $R_5$ group is a methyl group or an ethyl group; the $R_3$ and $R_4$ groups are, individually, hydrogen atoms or methyl groups; the $R_7$ group is a hydrogen atom, an ethyl group, or an amino containing group; and the $R_6$ group is a hydrogen atom.

The preferred R group substituents of the ketimine or aldimine alcohol compounds (I) of the present invention are also those which increase the reactivity of the compound to formaldehyde. The formaldehyde scavenging ketimine or aldimine alcohol compounds (I) of the present invention can react with formaldehyde and upon hydrolysis, will react with formaldehyde to form an oxazolidine reaction product. One mole of formaldehyde scavenging ketimine or aldimine alcohol will react with and remove one mole of formaldehyde. Therefore, it is preferred that the formaldehyde scavenging mixtures of the invention containing ketimine or aldimine alcohols include at least one mole of the formaldehyde scavenging ketimine or aldimine alcohol for each mole of formaldehyde to be removed from a preparation. However, since a perfectly efficient reaction environment cannot be guaranteed in industrial settings, it is preferable that from 1 to about 10 moles of the formaldehyde scavenging ketimine or aldimine alcohol be included for every mole of formaldehyde to be removed from a preparation. Some applications require that only from 1 to about 3 moles of the formaldehyde scavenging ketimine or aldimine alcohol be included for every mole of formaldehyde to be removed from the preparation. Greater amounts of the ketimine or aldimine alcohol can be added to reduce the viscosity and/or volatile organic content of the preparation. As much as 100 moles of the mixture may be required to effect the desired change in the physical properties of the preparation.

Referring to the oxazolidine compounds (II) of the present invention, the preferred R group substituents are those which increase the reactivity of the ring to water. Without limiting the invention, it has been discovered that amino containing $R_7$ substituents and aliphatic or aromatic R group substituents increase the reactivity of the ring to water. The moisture scavenging oxazolidine compounds (II) of the present invention react chemically with water in the following manner:

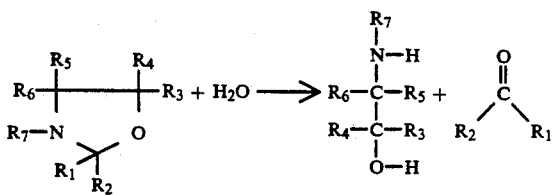

As shown above, the reaction products are an amino alcohol and a carbonyl compound. One mode of moisture scavenging oxazolidine compound (II) will react with and remove one mole of water. Therefore, it is preferred that the moisture scavenging mixtures of the invention containing oxazolidine compounds include at least one mole of the moisture scavenging oxazolidine compound for each mole of water to be removed from a preparation. However, since a perfectly efficient reaction environment cannot be guaranteed in industrial settings, it is preferable that from 1 to about 10 moles of the moisture scavenging oxazolidine compound be included for every mole of water to be removed from a preparation. Some applications require that only from 1 to about 3 moles of the moisture scavenging oxazolidine be included for every mole of water to be removed from the preparation. Greater amounts of the oxazolidine compound can be added to reduce the viscosity and/or volatile organic content of the preparation. As much as 100 moles of the mixture may be required to effect the desired change in the physical properties of the preparation.

All R group substituents which facilitate the reaction of water with the moisture scavenging oxazolidine compounds (II) of the present invention are preferred. In one preferred embodiment of the invention, the $R_7$ substituent of the compound (II) is a hydrogen atom, a methyl group, an ethyl group, a straight chain or branched chain alkyl group, an acyl group, an aryl group, an ester containing group, or an amino containing group, the $R_6$ substituent of the compound is a hydrogen atom or a methyl group; the $R_5$ substituent of the compound is a hydrogen atom, a methyl or ethyl group, or a ($C_3$-$C_5$) branched chain or straight chain alkyl group; the $R_3$ and $R_4$ groups are hydrogen atoms; the $R_1$ substituent is an aryl group, an ethyl group or a ($C_3$-$C_5$) branched or straight chain alkyl group; and the $R_2$ substituent is a hydrogen atom, a methyl group, an ethyl group, or a ($C_3$-$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$-$C_5$) branched or straight chain alkyl group; the $R_2$ and $R_5$ substituents are methyl or ethyl groups, or ($C_3$-$C_5$) branched or straight chain alkyl groups; the $R_7$ substituent is a hydrogen atom, a methyl group, an ethyl group, an acyl group, an aryl group, an ester containing group, or an amino containing group; the $R_3$ and $R_4$ groups are, individually, hydrogen atoms or methyl groups; and the $R_6$ group is a hydrogen atom. Most preferably, the $R_1$ substituent is an aryl group or a ($C_3$-$C_5$) branched or straight chain alkyl group; the $R_2$ substituent is a methyl group, an ethyl group, or a ($C_3$-$C_5$) branched or straight chain alkyl group; the $R_5$ group is a methyl group or an ethyl group; the $R_3$ and $R_4$ groups are, individually, hydrogen atoms or methyl groups; and the $R_7$ group is a hydrogen atom, an ester containing group, or an amino containing group; and the $R_6$ group is a hydrogen atom.

The preferred R group substituents of the oxazolidine compounds (II) of the present invention are also those which increase the reactivity of the compound to formaldehyde. The formaldehyde scavenging oxazolidine compounds (II) of the present invention react with formaldehyde when the $R_7$ substituent is a hydrogen atom. The reaction occurs regardless of the presence of water in the preparation from which the formaldehyde is to be removed. It is preferable that from 1 to about 10 moles of the formaldehyde scavenging oxazolidine be included for every mole of formaldehyde to be removed from a preparation. Some applications require that only from 1 to about 3 moles of the moisture scavenging oxazolidine be included for every mole of water to be removed from the preparation. Greater amounts of the oxazolidine can be added to reduce the viscosity and/or volatile organic content of the preparation. As much as 100 moles of the mixture may be required to effect the desired change in the physical properties of the preparation.

The structure of the R substituents in either the ketiminoalkanols, aldiminoalkanols or monocyclic oxazolidines is determined by the selection of the reactant precursor compounds. Reaction of a primary amino alcohol with a carbonyl compound produces an equilibrium mixture of an oxazolidine compound (II) along with its tautomeric iminoalcohol compound (I) as confirmed by IR spectral data. The amount of each compound present in the equilibrium mixture varies depending on the R substituents. Bulky substituents at $R_1$ and $R_2$, as well as substitution at $R_3$ and $R_4$ will generally shift the equilibrium to the iminoalcohol compound (I), although the compounds of the present invention are not limited thereto. In a specific embodiment of the invention, the 2-(1-hydroxybutyl) (4-methyl-2-pentylidine) amine/4-ethyl-2-methyl-2-(2-methylpropyl)1,3-oxazolidine iminoalcohol-oxazolidine mixture is prepared by reacting D,L-2-amino-1-butanol with methyl isobutyl ketone. Detailed protocols for synthesizing several preferred moisture scavengers of the present invention are described herein.

A further aspect of the invention is directed to a method of dehydrating a preparation. In one embodiment the preparation includes at least one pigment and at least one organic solvent. According to the method, an effective amount of the mixture of the present invention including a ketimine or aldimine alcohol and/or a monocyclic oxazolidine moisture scavenging compound as described above is intimately admixed with the preparation. In a preferred embodiment, the effective amount includes from 1 to about 10 moles of the mixture for every mole of water in the preparation to be dehydrated. Most preferably, from 1 to about 3 moles of the mixture is added to the preparation for every mole of water in the preparation to be dehydrated.

According to one embodiment of the invention, catalysts are added in combination with the iminoalcohol-oxazolidine mixtures of the present invention to facilitate the reaction with water. The addition of a preferred catalyst will, in some instances, minimize the amount of the iminoalcohol-oxazolidine mixture required to remove water from a preparation by increasing the efficiency of the reaction. Furthermore, a preferred catalyst will, in certain circumstances, increase the rate at which the moisture scavenging compounds react with water. Preferred catalysts include the organometallic catalysts, such as dibutyltin dilaurate, the mineral acid catalysts and the organic acid catalysts, such as acetic acid.

According to another embodiment of the invention, the reaction between the moisture scavenging compounds and water occurs at temperatures from ambient to about the boiling point of the preparation being dehydrated. Preferably, this range is from about 40 to about 180 degrees Fahrenheit. Increasing the temperature at which the reaction occurs increases the rate and the efficiency of the reaction.

The moisture scavenging compounds of the present invention are advantageously used in preparations including urethane coating, sealant and adhesive systems to remove moisture during the formulation, packaging and application steps. The present invention provides the producer of specialty polyurethane systems with an expedient and efficient alternative to the physical methods of dehydration, exemplified by molecular sieves and drying machinery, and the potentially toxic prior chemical methods, exemplified by the monomeric isocyanates presently available. The compounds also provide the coatings with improved consistency and application properties by improving the solvency effects (i.e., the degree to which a solvent holds a resin or other paint binder in solution) in the urethane coatings. The moisture scavenging compounds of the present invention are further provided for the storage stabilization of moisture curable polyurethane systems. A still further intended use of the invention is the dehydration of surfaces onto which moisture curable coatings are to be applied. Furthermore, the compounds improve the pot life of two component polyurethane coating systems.

The compounds of the present invention are also useful in scavenging moisture from radiation cure coatings such as UV cure coatings. The addition of the moisture scavenging mixture to a radiation cure coating reduces hazing, cloudiness and brittleness that is caused by the presence of moisture. The moisture scavenging compounds also act as a reactive diluent in reducing the volatile organic content to impart improved flow and film properties to the coating.

Composites and gasses are also dried using the compounds of the present invention. Composites are elastomers which are considerably thicker than films, such as sealants, construction materials, shoe soles, extruded plastics, and aerospace panels. Composites, like urethane coatings, may be adversely affected by water prior to curing. The moisture scavenging compounds are added to a composite prior to curing to reduce brittleness of the elastomer which results from moisture. Gasses are dehumidified for use in industrial processes through the use of the moisture scavenging compounds. For example, forced air flow over a urethane coating serves to dehumidify the air.

The moisture scavenging compounds are also useful in drying inks. During the process of forming an ink, a pigment slurry is commonly mixed with resins or vehicles to drive water out of the slurry. After this flushing stage, any residual water is removed by subjecting the ink to a two to six hour vacuum stripping process. The compounds of the present invention are added to the slurry either alone or with a resin to scavenge the water from the ink after flushing of the ink so that the conventional vacuum stripping process can be eliminated or minimized.

The invention provides an anhydrous composition including the moisture scavenging compounds described above and an organic solvent. Solvents used in the formulation of one and two-component systems are rapidly dehydrated by treating them with the moisture scavenging mixture of the invention. This anhydrous composition is useful in any application where water is preferably avoided, e.g., preparing moisture curable polyurethane coatings, or dehydrating surfaces prior to applying moisture curable coatings. The quantity of moisture scavenger in the composition will vary with the water content of the solvent. The amount of water in the organic solvent being dehydrated can be determined by gas chromatography or Karl Fischer technique. The solvents generally used in the formulation of specialty polyurethane systems are compatible with the moisture scavenging compositions of the present invention. Solvents generally used in the preparation of polyurethane moisture scavenging preparations include aprotic solvents, such as ketones, esters, ethers, nitroparaffins, glycol esters, glycol ether esters, halogenated hydrocarbons, and alkyl and aromatic hydrocarbons.

Pigments, fillers, polyisocyanates, and adjuvants are suspended in organic solvents. For the purposes of this invention the term "fillers" is intended to include those materials added to a coating preparation to increase the solids content of the coating. The term "adjuvants" is intended to include those materials which are added to the coating formulation to aid application or formation, such as surface active agents, anti-settling agents, diluents, suspending agents, dispersants, flow additives, UV inhibitors and the like. Pigments, fillers, polyisocyanates and adjuvants can also be dehydrated with the water scavenging compositions of the present invention. Sacrificial pigments, for example, are added to coatings so that the pigment will corrode for the sake of protecting an underlying metal substrate from corrosion. Conventional sacrificial pigments include chromium oxide, zinc oxide, and strontium oxide. The addition of the moisture scavenging compounds of the present invention to the sacrificial pigment prevent corrosion of the pigment prior to its use in a coating formulation.

One aspect of the present invention is a substantially anhydrous composition including pigments, fillers, organic solvents, and the moisture scavenging compounds described above. It has been determined that a reaction period of from 30 minutes to about twenty-four hours is preferred to ensure substantially complete dehydration of pigment preparations. The amount of the moisture scavenger composition required to dehydrate the pigment or filler will vary with the total water content. Through the addition of the moisture scavenging composition of the invention, an anhydrous composition is produced including pigments, organic solvents, fillers, polyisocyanates and adjuvants. Alternatively, any of the above-listed components can be deleted, depending on the needs of the ultimate user. This anhydrous composition is useful in applications where water is preferably avoided, e.g., in the formulation of moisture curable polyurethane coatings.

A further aspect of the invention is directed to a method of scavenging formaldehyde from a preparation. In one embodiment, the preparation is a phenol-formaldehyde, urea-formaldehyde, or melamine-formaldehyde polymeric system. According to the method, an effective amount of the mixture of the present including a ketimine or aldimine alcohol and/or a monocyclic oxazolidine formaldehyde scavenging compound as described above is intimately admixed with the preparation. An effective amount is an amount of the mixture which removes free formaldehyde in the preparation. In a preferred embodiment, the effective amount includes from 1 to about 10 moles of the mixture for every mole of formaldehyde in the preparation. Most preferably, from 1 to about 3 moles of the mixture is added to the preparation for every mole of formaldehyde in the preparation. The compounds of the present invention will scavenge formaldehyde regardless of the presence of water in the preparation. However, the presence of a catalyst or water may facilitate the reaction of the oxazolidine compound with formaldehyde.

Another aspect of the present invention is directed to a method of inhibiting corrosion of a metal or alloy. According to the method, an effective amount of the mixture of the present invention including a ketimine or aldimine alcohol and/or a monocyclic oxazolidine corrosion inhibiting compound as described above contacts the surface of a metal or alloy. An effective amount is an amount of the mixture sufficient to prevent the formation of corrosion in a preparation. In one embodiment, the mixture is applied directly to the metal or alloy by coating the metal or alloy with the mixture. Alternatively, the mixture may be incorporated into a paint formulation or other coating formulation which is to be applied to the metal or alloy. In a second embodiment, the mixture is intimately admixed with a functional fluid which contacts a metal or alloy. The term "functional fluid" is defined for purposes of the present invention to include any industrial fluid such as a lubricant, hydraulic fluid, hydrocarbon fuel or jet fuel. Additional examples of functional fluids include but are not limited to transmission fluid, motor oil, gasoline, diesel fuel, kerosene, greases, and synthetic oils such as polyethylene oils, polysilicones, fluorohydrocarbon oils, and esters of dicarboxylic acids, polyglycol and alcohol. The functional fluid may also be an aqueous system such as a cooling water system, an air conditioning system, or a steam generating system. In a preferred embodiment, the effective amount includes from 1 to about 10 moles of the mixture for every mole of water in the functional fluid. Most preferably, from 1 to about 3 moles of the mixture is added to the preparation for every mole of water in the functional fluid.

Yet another aspect of the present invention is directed to a method for preventing the formation of ice crystals and for lowering the freezing point of an industrial fluid while removing moisture from the preparation. Conversely, conventional antifreezing agents lower the freezing point of an industrial fluid without removing moisture from the fluid. According to the method of the invention, an effective amount of the mixture of the present invention including a ketimine or aldimine alcohol and/or a monocyclic oxazolidine compound as described above is intimately admixed with an industrial fluid which may be exposed to low temperatures during use in automobiles, airplanes or other machinery. An effective amount is an amount of the mixture which prevents an industrial fluid from freezing. The term "industrial fluid" is defined for the purposes of this invention to include any lubricant, hydraulic fluid, hydrocarbon fuel, jet fuel and the like. In a preferred embodiment, the effective amount includes from 1 to about 10 moles of the mixture for every mole of water in the industrial fluid. Most preferably, from 1 to about 3 moles of the mixture is added to the preparation for every mole of water in the industrial fluid. If the preparation does not contain water, the effective amount of the mixture is from 1 to about 30 wt. % of the mixture based on the total weight of the preparation. Most preferably, from 1 to about 10 wt. % of the mixture based on the total weight of the preparation is added to the preparation.

A further aspect of the present invention is directed to a method of reducing volatile organic content and a concentration of an active material in a preparation and improving rheological properties of the preparation using a reactive diluent. An active material is a component of the preparation which is reactive with polyisocyanate or water. In one embodiment, the active material is a polyol or prepolymer which is a component of a coating, adhesive, sealant, epoxy, radiation cure coating, or ink preparation. The mixture of the present invention is substituted for the volatile organic solvents and reacts to form a part of the preparation. The mixture acts to form a high solids preparation while reducing the release of volatile organics into the atmosphere. According to the method, an effective amount of the mixture of the present invention including a ketimine or aldimine alcohol and/or a monocyclic oxazolidine reactive diluent compound as described above is intimately admixed with the preparation. An effective amount is an amount of the mixture sufficient to reduce the viscosity and volatile organic content of the preparation and provide an acceptable potlife or stability and cure rate while improving the film properties of the preparation. In a preferred embodiment, the effective amount includes from 1 to about 30 weight percent of the mixture based on the total weight of the preparation. Most preferably, from 1 to about 10 weight percent of the mixture based on the total weight of the preparation is added. Film properties which may be improved by the mixture of the present invention include, but are not limited to, gloss, hardness, impact resistance, flexibility, chemical resistance, abrasion resistance, exterior durability, humidity and salt fog resistance.

Another aspect of the present invention is directed to a method of obtaining a stable dispersion, suspension or solution. According to the method, an effective amount of the mixture of the present invention including a ketimine or aldimine alcohol and/or a monocyclic oxazolidine stabilizing compound as described above is intimately admixed with the dispersion, suspension or solution. An effective amount is an amount of the mixture which provides sufficient solvency or pigment dispersability. Solvency is the ability of an additive to hold a resin or other binder in solution. Dispersability is the ability of an additive to increase the stability of a suspension of pigments in a liquid medium. In a preferred embodiment, the effective amount includes from 1 to about 30 weight percent of the mixture based on the total weight of the dispersion, suspension or solution. Most preferably, from 1 to about 10 weight percent of the mixture based on the total weight of the dispersion, suspension or solution is added.

Another aspect of the invention is directed to a method of reducing the foaming of a thermoplastic to improve processing and quality of the thermoplastic. Foaming during formation of urethane and urethane/polyurea thermoplastics is produced by the formation of carbon dioxide from the reaction of water with an isocyanate. According to the method, an effective amount of the mixture of the present invention including a ketimine or aldimine alcohol and/or a monocyclic oxazolidine foam inhibiting compound as described above is intimately admixed with the thermoplastic. An effective amount is an amount of the mixture which will react with water in the thermoplastic to prevent the formation of carbon dioxide. In a preferred embodiment, the effective amount includes from 1 to about 10 moles of the mixture for every mole of water in the thermoplastic. Most preferably, from 1 to about 3 moles of the mixture is added to the thermoplastic for every mole of water in the thermoplastic.

A further aspect of the invention is directed to a method of modifying the rheology of a preparation. Rheology is the deformation and flow of the preparation. Rheological properties which may be modified by the mixture of the present invention include sagging, flow and film build. In an embodiment of the method, the preparation is a coating, adhesive or sealant which has improved flow and film properties as a result of reduced viscosity. According to the method, an effective amount of the mixture of the present invention including a ketimine or aldimine alcohol and/or a monocyclic oxazolidine compound as described above is intimately admixed with the preparation. An effective amount is an amount of the mixture which is sufficient to reduce the viscosity and improve the rheological properties of the preparation. In a preferred embodiment, the effective amount includes from 1 to about 30 weight percent of the mixture based on the total weight of the preparation. Most preferably, from 1 to about 10 weight percent of the mixture based on the total weight of the preparation is added. Although the mixture can be added to the preparation at any stage, it is most common to add the mixture during the grind phase and/or the let down phase. When the mixture is added during the grind phase, the mixture also acts as a pigment dispersant to prevent agglomerate formation. Accordingly, addition of the mixture to a coating, adhesive or sealant assures that the pigment particles are finely divided and stabilized.

Another aspect of the invention is directed to a method of decolorizing a preparation. According to the method, an effective amount of the mixture of the present invention including a ketimine or aldimine alcohol and/or a monocyclic oxazolidine decolorizing compound as described above is intimately admixed with the preparation. An effective amount is an amount of the mixture which will sufficiently remove the color from a preparation. In a preferred embodiment, the effective amount includes from 1 to about 30 weight percent of the mixture based on the total weight of the preparation. Most preferably, from 1 to about 10 weight percent of the mixture based on the total weight of the preparation is added. The preparations which may be decolorized include phenols and amines.

Greater amounts of the mixture can be added in the methods of the present invention to reduce the viscosity and/or volatile organic content of the preparation. In excess of 100 moles of the mixture for every mole of water or formaldehyde in a preparation may be required to effect the desired change in the physical properties of the preparation. Likewise, in excess of 50 weight percent of the mixture based on the total weight of the preparation may be required in decolorant, antifreeze, reactive diluent or rheological modifier applications.

The following examples are presented to describe preferred embodiments and utilities of the present invention and are not meant to limit the present invention unless otherwise stated in the claims appended hereto. Each of the equilibrium mixtures is referred to in the examples by the name of the iminoalcohol compound present in the mixture. These iminoalcohol compounds and their corresponding oxazolidines which form equilibrium mixtures are listed in the table below.

TABLE 1

| Iminoalcohol-Oxazolidine Mixtures of the Present Invention | |
|---|---|
| Iminoalcohol | Oxazolidine |
| 2-(1-hydroxybutyl) (cyclohexylidine) amine | 4-ethyl-1,3-oxazolidine-2-spiro-1'-cyclohexane |
| 2-(1-hydroxy-2-hydroxymethylbutyl) (cyclohexylidine) amine | 4-ethyl-4-hydroxymethyl-1,3-oxazolidine-2-spiro-1'-cyclohexane |
| 2-(1-hydroxybutyl) (4-methyl-2-pentylidine) amine | 4-ethyl-2-methyl-2-(2-methylpropyl)-1,3-oxazolidine |
| 2-(1-hydroxy-2-hydroxymethylbutyl) (4-methyl-2-pentylidine) amine | 4-ethyl-4-hydroxymethyl-2-methyl-2-(2-methylpropyl)-1,3-oxazolidine |
| 2-(1-hydroxybutyl) (1-phenyl-1-ethylidine) amine | 4-ethyl-2-methyl-2-phenyl-1,3-oxazolidine |
| 2-(1-hydroxy-2-hydroxymethylbutyl) (1-phenyl-1-ethylidine) amine | 4-ethyl-4-hydroxymethyl-2-methyl-2-phenyl-1,3-oxazolidine |
| 2-(1-hydroxybutyl) (2-heptylidine) amine | 4-ethyl-2-methyl-2-pentyl-1,3-oxazolidine |
| 2-(1-hydroxy-2-hydroxymethylbutyl) (2-heptylidine) amine | 4-ethyl-4-hydroxymethyl-2-methyl-2-pentyl-1,3-oxazolidine |
| 2-(1-hydroxybutyl) | 4-ethyl-2-methyl-2-(3-methyl- |

TABLE 1-continued

Iminoalcohol-Oxazolidine Mixtures of the Present Invention

| Iminoalcohol | Oxazolidine |
|---|---|
| (5-methyl-2-hexylidene) amine | butyl)-1,3-oxazolidine |
| 2-(1-hydroxy-2-hydroxy-methylbutyl)(5-methyl-2-hexylidene) amine | 4-ethyl-4-hydroxymethyl-2-methyl-2-(3-methylbutyl)-1,3-oxazolidine |
| 2-(1-hydroxybutyl)(2,6-dimethyl-4-heptylidene) amine | 2,2-(di-2-methylpropyl)-4-ethyl-1,3-oxazolidine |
| 2-(1-hydroxy-2-methylpropyl)(4-methyl-2-pentylidene) amine | 2-(2-methylpropyl)-2,4,4-trimethyl-1,3-oxazolidine |
| 2-(1,3-dihydroxy-2-methyl-propyl)(4-methyl-2-pentylidene) amine | 4-hydroxymethyl-2,4-dimethyl-2-(2-methylpropyl)-1,3-oxazolidine |
| 1-(2-hydroxypropyl)(5-methyl-2-hexylidene) amine | 2,5-Dimethyl-2-(3-methylbutyl)-1,3-oxazolidine |
| — | N-(5-Methyl-2-hexylidene aminoethyl)-2-methyl-2-(5-methylpentyl)-1,3-oxazolidine |

EXAMPLES

EXAMPLE 1

Preparation of 2-(1-Hydroxybutyl)(cyclohexylidene) amine/4-Ethyl-1,3-oxazolidine-2-spiro-1'-cyclohexane Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, cyclohexanone (161.9 grams; 1.6 mol.) was added over a ten minute period resulting in an exothermic reaction (26° C.→65° C.). The reaction mixture was heated to reflux and 24 grams of water were collected in the Dean-Stark trap over a two hour period. The product was purified by vacuum distillation (77°–78° C. at 3.5 mm Hg) using a mirrored column (250 mm×10 mm i.d.) packed with metal helixes. The material was stored under a nitrogen atmosphere.

EXAMPLE 2

Preparation of 2-(1-Hydroxy-2-hydroxymethylbutyl)(cyclohexylidene) amine/4-Ethyl-4-hydroxymethyl-1,3-oxazolidine-2-spiro-1'-cyclohexane Mixture 2-Amino-2-ethyl-1,3-propanediol (AEPD®) (178.9 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, cyclohexanone (309.1 grams; 3.1 mol.) was added over a seven minute period causing a lower reaction mixture temperature. The reaction mixture was heated to reflux and 25 grams of water were collected in the Dean-Stark trap over a two hour period. The product was purified by vacuum distillation (121° C.–123° C. at 2 mm Hg) using a mirrored column (250 mm×10 mm i.d.) packed with metal helixes. The material was stored under a nitrogen atmosphere.

EXAMPLE 3

Preparation of 2-(1-Hydroxybutyl)(4-methyl-2-pentylidene) amine/4-Ethyl-2-methyl-2-(2-methylpropyl)-1,3-oxazolidine Mixture D,L-2-Amino-1-butanol (AB®) (133.7 grams; 1.5 mol.) was added to a 3-neck, 500 ml. round bottom flask equipped with a magnetic stir bar, a 250 ml addition funnel, a thermometer, and a Dean-Stark trap (50 ml capacity). While stirring, 4-methyl-2-pentanone (MIBK) (165.3 grams; 1.6 mol.) was added over a three minute period causing a lower reaction mixture temperature. (20° C.→17° C.). The reaction mixture was heated to reflux and 25 grams of water were collected in the Dean-Stark trap over a six hour period. The crude product was purified by vacuum distillation (91° C. at 14 mm Hg) using a mirrored column (250 mm×10 mm i.d.) packed with metal helixes. The material was stored under a nitrogen atmosphere.

EXAMPLE 4

Preparation of 2-(1-Hydroxy-2-hydroxymethylbutyl)(4-methyl-2-pentylidene) amine/4-Ethyl-4-hydroxymethyl-2-methyl-2-(2-methylpropyl)-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 4-methyl-2-pentanone (MIBK) (315.7 grams; 3.1 mol.) was added over a three minute period causing the reaction mixture temperature to lower by 1° C. The reaction mixture was heated to reflux and 24 grams of water were collected in the Dean-Stark trap over a fifty-five hour period. The crude product was purified by vacuum distillation (107° C.–109° C. at 2 mm Hg) using a mirrored column (250 mm×10 mm i.d.) packed with metal helixes. The material was stored under a nitrogen atmosphere.

EXAMPLE 5

Preparation of 2-(1-Hydroxybutyl)(1-phenyl-1-ethylidene) amine/4-Ethyl-2-methyl-2-phenyl-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml. addition funnel, a thermometer, and a Dean-Stark trap (50 ml capacity). While stirring, acetophenone (198.3 grams; 1.6 mol.) was added over a five minute period causing a lower reaction mixture temperature (21° C. →18° C.). The reaction mixture was heated to reflux and 26 grams of water were collected in the Dean-Stark trap over a twenty hour period. The crude product was purified by a vacuum distillation (95°–99° at 2–3 mm Hg) using a mirrored column (250 mm×10 mm i.d.) packed with metal helixes. The material was stored under a nitrogen atmosphere.

EXAMPLE 6

Preparation of 2-(1-Hydroxy-2-hydroxymethylbutyl)(1-phenyl-1-ethylidene) amine/4-Ethyl-4-hydroxymethyl-2-methyl-2-phenyl-1,3-oxazolidine Mixture 2-Amino-2-ethyl-1,3-propanediol (AEPD®) (179.4 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, acetophenone (378.7 grams; 3.1 mol.) was added over an eight minute period causing a three degree lowering in the reaction mixture temperature. The reaction mixture was heated to reflux and 20 grams of water were collected in the Dean-Stark trap over a twenty hour period. The crude product was purified by vacuum distillation (114° C. →120° C. at 0.9-1.0 mm Hg) using a mirrored column (250 mm×10 mm i.d.) packed with metal helixes. The material was stored under a nitrogen atmosphere.

EXAMPLE 7

Preparation of 2-(1-Hydroxybutyl)(2-heptylidine) amine/4-Ethyl-2-methyl-2-pentyl-1,3-oxazolidine Mixture D,L-2-amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 2-heptanone (MAK) (188.3 grams; 1.6 mol.) was added over a three minute period causing a lowering of the reaction mixture temperature (24° C.→20° C.). The reaction mixture was heated to reflux and 24 grams of water were collected in the Dean-Stark trap over a thirteen hour period. The crude product was purified by vacuum distillation (70°-73° C. at 0.8-1.0 mm Hg) using a mirrored column (250 mm×10 mm i.d.) packed with metal helixes. The material was stored under a nitrogen atmosphere.

EXAMPLE 8

Preparation of 2-(1-Hydroxy-2-hydroxymethylbutyl)(2-heptylidine) amine/4-Ethyl-4-hydroxymethyl-2-methyl-2-pentyl-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 2-heptanone (MAK) (359.6 grams; 3.1 mol.) was added over a five minute period causing a two degree temperature drop in the reaction mixture temperature (24° C.→22° C.). The reaction mixture was heated to reflux and 26 grams of water were collected in the Dean-Stark trap over a thirteen hour period. The crude product was purified by vacuum distillation (97° C.-98° C. at 1.0 mm Hg) using a mirrored column (250 mm×10 mm i.d.) packed with metal helixes. The material was stored under a nitrogen atmosphere.

EXAMPLE 9

Preparation of 2-(1-Hydroxybutyl)(5-methyl-2-hexylidine) amine/4-Ethyl-2-methyl-2-(3-methylbutyl)-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 5-methyl-2-hexanone (MIAK) (188.4 grams; 1.6 mol.) was added over a four minute period causing a four degree lowering of the reaction mixture temperature (22° C.→18° C.). The reaction mixture was heated to reflux and 21 grams of water were collected in the Dean-Stark trap over a twelve hour period. The crude product was purified by vacuum distillation (46°-48° C. at 0.3 mm Hg) using a mirrored column (250 mm×10 mm i.d.) packed with metal helixes. The material was stored under a nitrogen atmosphere.

EXAMPLE 10

Preparation of 2-(1-Hydroxy-2-hydroxymethylbutyl)(5-methyl-2-hexylidine) amine/4-Ethyl-4-hydroxymethyl-2-methyl-2-(3-methylbutyl)-1,3-oxazolidine Mixture 2-Amino-2-ethyl-1,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 5-methyl-2-hexanone (MIAK) (360.0 grams; 3.1 mol.) was added over a three minute period causing a one degree temperature drop in the reaction mixture temperature (22° C.→21° C.). The reaction mixture was heated to reflux and 25 grams of water were collected in the Dean-Stark trap over a ten hour period. The crude product was purified by vacuum distillation (98°-99° C. at 0.3 mm Hg) using a mirrored column (250 mm×10 mm i.d.) packed with metal helixes. The material was stored under a nitrogen atmosphere.

EXAMPLE 11

Preparation of 2-(1-Hydroxybutyl)(2,6-dimethyl-4-heptylidine) amine/2,2-(Di-2-methylpropyl)-4-ethyl-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 2,6-dimethyl-4-heptanone (DIBK) (234.7 grams; 1.3 mol.) was added over a two minute period causing a three degree lowering of the reaction mixture temperature (24° C.→21° C.). The reaction mixture was heated to reflux and 24 grams of water were collected in the Dean-Stark trap over a twenty hour period. The crude product was purified by vacuum distillation (95°-99° C. at 1.5-1.8 mm Hg) using a mirrored column (250 mm×10 mm i.d.) packed with metal helixes. The material was stored under a nitrogen atmosphere.

EXAMPLE 12

Preparation of 2-(1-Hydroxy-2-methylpropyl)(4-methyl-2-pentylidine) amine/2-(2-Methylpropyl)-2,4,4-trimethyl-1,3-oxazolidine Mixture 2-Amino-2-methyl-1-propanol (AMP TM) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). The flask was warmed to 45° C. to melt the AMP TM. While stirring, 4-methyl-2-pentanone (MIBK) (165.3 grams; 1.6 mol.) was added over a five minute period and the mixture was heated to reflux. After thirty-five hours, 23 grams of water were collected in the Dean-Stark trap. The crude product was purified by vacuum distillation (36° C. at 1.1 mm Hg) using a mirrored column (250 mm×10 mm i.d.) packed with metal helixes. The material was stored under a nitrogen atmosphere.

EXAMPLE 13

Preparation of
2-(1,3-Dihydroxy-2-methylpropyl)(4-methyl-2-pentylidine)
amine/4-Hydroxymethyl-2,4-dimethyl-2-(2-methylpropyl)-1,3-oxazolidine Mixture 2-Amino-2-methyl-1,3-propanediol (AMPD TM) (157.7 grams; 1.5 mol.) was added to a 3-neck, 1 liter round bottom flask equipped with a mechanical stirrer, a 500 ml addition funnel, a thermometer, and a Dean-Stark trap (100 ml capacity). The flask was warmed to 115° C. to melt the AMPD TM. While stirring, 4-methyl-2-pentanone (MIBK) (180.3 grams; 1.8 mol.) was added gradually over a twenty-two minute period to prevent lowering the temperature and precipitation of the AMPD TM. The mixture was heated to reflux and after twenty-six hours, 24 grams of water were collected in the Dean-Stark trap. The crude product was purified by vacuum distillation (95° C.–100° C. at 1.8–2.0 mm Hg) using a mirrored column (250 mm × 10 mm i.d.) packed with metal helixes. The material was stored under a nitrogen atmosphere.

EXAMPLE 14

Preparation of
1-(2-Hydroxypropyl)(5-methyl-2-hexylidine)
amine/2,5-Dimethyl-2-(3-methylbutyl)-1,3-oxazolidine Monoisopropanolamine (MIPA) (118.6 grams; 1.58 mol.) was added to a 3-neck, 500 ml round bottom flask equipped with a mechanical stirrer, a 125 ml addition funnel, a thermometer, and a Dean-Stark trap (20 ml capacity). While stirring, 5-methyl-2-hexanone (MIAK) (202.4 grams; 1.76 mol.) was added over a 5 minute period causing a lower reaction mixture temperature. The reaction mixture was heated to reflux and 29 grams of water were collected in the Dean-Stark trap over a 2 hour period. The product was purified by vacuum distillation (85° C.–90° C. at 15 mm Hg) using a mirrored column (250 mm × 10 mm i.d.) packed with metal helixes. The material was stored under a nitrogen atmosphere.

EXAMPLE 15

Preparation of N-(5-Methyl-2-hexylidine
aminoethyl)-2-methyl-2-(5-methylpentyl)-1,3-oxazolidine Aminoethyl ethanolamine (AEEA) (104.2 grams; 1.00 mol.) was added to a 4-neck, 500 ml round bottom flask equipped with a mechanical stirrer, a 250 ml addition funnel, a thermometer, and a Dean-Stark trap (20 ml capacity). While stirring, 5-methyl-2-hexanone (MIAK) (262 grams; 2.29 mol.) was added over a 10 minute period causing a lower reaction mixture temperature. The reaction mixture was heated to reflux and 25.8 grams of water were collected in the Dean-Stark trap over a 3 hour period. The product was purified by vacuum distillation (143° C.–148° C. at 5 mm Hg) using a 10 in. Vigreaux column. The material was stored under a nitrogen atmosphere.

EXAMPLE 16

Water Hydrolysis Comparison Study

The appropriate amount of an iminoalcohol-oxazolidine mixture (0.02 mol.) was added to a 100 ml volumetric flask and was diluted with some acetonitrile. Five equivalents of water (0.10 mol., 1.8 grams) and a 10 mole % catalyst load of acetic acid based on the iminoalcohol-oxazolidine mixture (0.002 mol., 0.12 grams) were added to the solution. The solution was then diluted to the mark on the volumetric flask with acetonitrile. The amount of iminoalcohol-oxazolidine mixture, acetic acid and water for each solution that was prepared are listed below in Table 2.

TABLE 2

| Iminoalcohol-oxazolidine Mixture | Iminoalcohol-oxazolidine Mixture (Grams) | HOAc (Grams) | Water (Grams) |
|---|---|---|---|
| 2-(1-Hydroxybutyl) (cyclohexylidine) amine | 3.38 | 0.12 | 1.8 |
| 2-(1-Hydroxy-2-hydroxymethylbutyl) (cyclohexylidine) amine | 3.98 | 0.12 | 1.8 |
| 2-(1-Hydroxybutyl) (4-methyl-2-pentylidine) amine | 3.42 | 0.12 | 1.8 |
| 2-(1-Hydroxy-2-hydroxymethylbutyl) (4-methyl-2-pentylidine) amine | 4.02 | 0.12 | 1.8 |
| 2-(1-Hydroxybutyl) (1-phenyl-1-ethylidine) amine | 3.82 | 0.12 | 1.8 |
| 2-(1-Hydroxy-2-hydroxymethylbutyl) (1-phenyl-1-ethylidine) amine | 4.42 | 0.12 | 1.8 |
| 2-(1-Hydroxybutyl) (2-heptylidine) amine | 3.70 | 0.12 | 1.8 |
| 2-(1-Hydroxy-2-hydroxymethylbutyl) (2-heptylidine) amine | 4.30 | 0.12 | 1.8 |
| 2-(1-Hydroxybutyl)(5-methyl-2-hexylidine) amine | 3.70 | 0.12 | 1.8 |
| 2-(1-Hydroxy-2-hydroxymethylbutyl) (5-methyl-2-hexylidine) amine | 4.30 | 0.12 | 1.8 |
| 2-(1-Hydroxybutyl) (2,6-dimethyl-4-heptylidine) amine | 4.26 | 0.12 | 1.8 |
| 2-(1-Hydroxy-2-methylpropyl) (4-methyl-2-pentylidine) amine | 3.42 | 0.12 | 1.8 |

After the solution was prepared, samples of the solution were held at 60° C. and monitored by gas chromatography every twenty-four minutes for the iminoalcohol-oxazolidine mixture, amino alcohol and ketone content over an eight hour period. A normalized gas chromatographic area count was determined for the above three components. A potential water scavenger candidate was determined by the decrease in iminoalcohol-oxazolidine mixture content with a corresponding appearance of the amino alcohol and ketone content. A graphical representation of the data is made by plotting the normalized peak areas of iminoalcohol, oxazolidine, amino alcohol, and ketone versus time (minutes).

Figure 2:
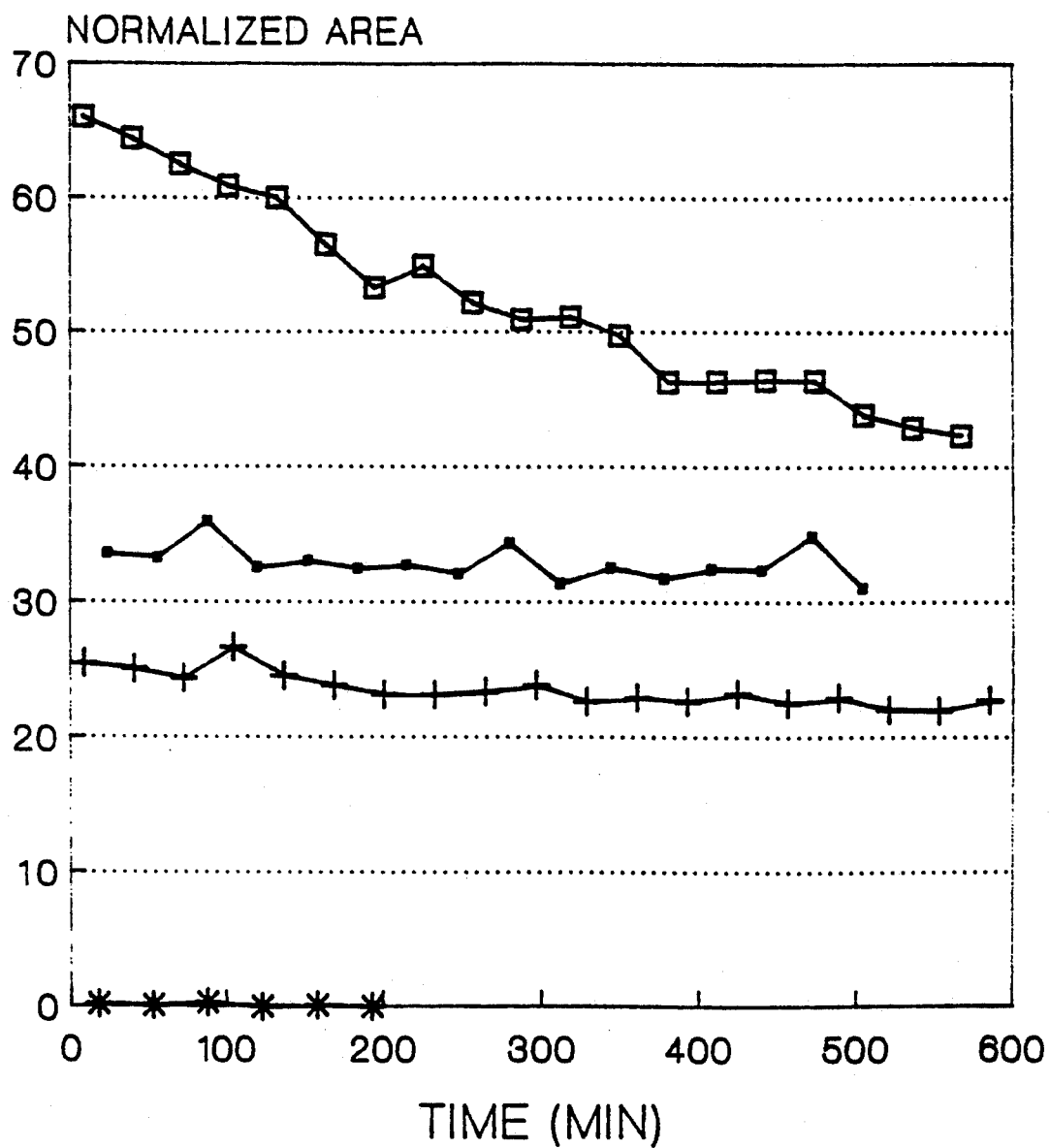
FIG. 2 graphically illustrates the relative hydrolysis rates of the 2-(1-hydroxybutyl)(cyclohexylidine) amine/4-ethyl-1,3-oxazolidine-2-sprio-1'-cyclohexane mixture (-··-), the 2-(1-hydroxybutyl)(4-methyl-2-pentylidine) amine/4-ethyl-2-methyl-2-(2-methylpropyl)-1,3-oxazolidine mixture (-*-), the 2-(1-hydroxy-2-hydroxymethylbutyl)(4-methyl-2-pentylidine) amine/4-ethyl-4-hydroxymethyl-2-methyl-2-(2-methylpropyl)-1,3-oxazolidine mixture (-+-), and the 2-(1-hydroxy-2-hydroxymethylbutyl)(2-heptylidine) amine/4-ethyl-4-hydroxymethyl-2-methyl-2-pentyl-1,3-oxazolidine mixture (-□-)

Relative hydrolysis rates of most of the above listed iminoalcohol-oxazolidine mixtures are compared in FIGS. 1 and 2 which show the normalized peak areas of the oxazolidine versus time. The 2-(1-hydroxybutyl)(4-methyl-2-pentylidine) amine mixture, 2-(1-hydroxybutyl)(2,6-dimethyl-4-heptylidine) amine mixture, 2-(1-hydroxybutyl)(2-heptylidine) amine mixture, 2-(1-hydroxybutyl)(5-methyl-2-hexylidine) amine mixture and 2-(1-hydroxybutyl)(1-phenyl-1-ethylidine) amine mixture are shown to have greater hydrolysis rates than the other iminoalcohol-oxazolidine mixtures which were considered. The iminoalcohol-oxazolidine mixture having the most preferred hydrolysis rate is the 2-(1-hydroxybutyl)(4-methyl-2-pentylidine) amine mixture.

EXAMPLE 17

Comparison of Water Scavenging Activity

The appropriate amount of an iminoalcohol-oxazolidine mixture (0.02 mol.) was added to a 100 ml volumetric flask and diluted with some acetonitrile. A half an equivalent of water (0.01 mol., 0.18 gram) and a 10 mole % catalyst load of acetic acid (0.002 mol., 0.12 gram) were added to the solution. The solution was then diluted to the mark on the volumetric flask with acetonitrile. The amount of iminoalcohol-oxazolidine mixture, acetic acid and water for each solution that was prepared are listed below in Table 3.

TABLE 3

| Iminoalcohol-oxazolidine Mixture | Iminoalcohol-oxazolidine Mixture (Grams) | HOAc (Grams) | Water (Grams) |
| --- | --- | --- | --- |
| 2-(1-Hydroxybutyl)(4-methyl-2-pentylidine) amine | 3.4313 | 0.1229 | 0.1851 |
| 2-(1-Hydroxybutyl)(1-phenyl-1-ethylidine) amine | 3.8276 | 0.1280 | 0.1847 |
| 2-(1-Hydroxybutyl)(2-heptylidine) amine | 3.7129 | 0.1233 | 0.1828 |
| 2-(1-Hydroxybutyl)(5-methyl-2-hexylidine) amine | 3.7109 | 0.1235 | 0.1831 |
| 2-(1-Hydroxybutyl)(2,6-dimethyl-4-heptylidine) amine | 4.2753 | 0.1249 | 0.1822 |
| 2-(1-Hydroxy-2-methylpropyl)(4-methyl-2-pentylidine) amine | 3.4305 | 0.1225 | 0.1850 |

Figure 3:
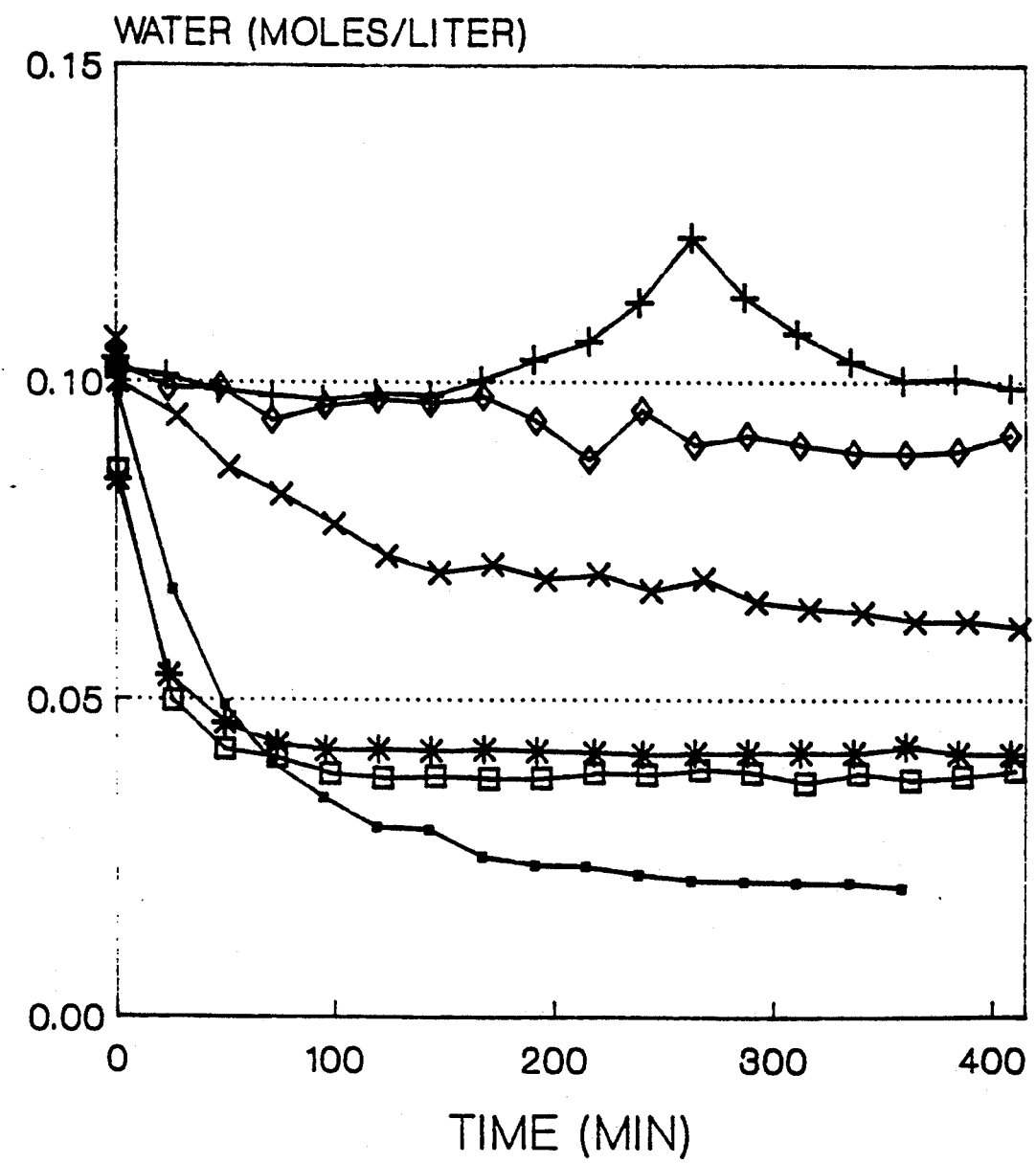
FIG. 3 graphically illustrates the relative water scavenging activity of the 2-(1-hydroxybutyl)(4-methyl-2-pentylidine) amine/4-ethyl-2-methyl-2-(2-methylpropyl)-1,3-oxazolidine mixture (-··-), the 2-(1-hydroxybutyl)(1-phenyl-1-ethylidine) amine/4-ethyl-2-methyl-2-phenyl-1,3-oxazolidine mixture (-+-), the 2-(1-hydroxybutyl)(2-heptylidine) amine/4-ethyl-2-methyl-2-pentyl-1,3-oxazolidine mixture (-*-), the 2-(1-hydroxybutyl)(5-methyl-2-hexylidine) amine/4-ethyl-2-methyl-2-(3-methylbutyl)-1,3-oxazolidine mixture (-□-), the 2-(1-hydroxybutyl)(2,6-dimethyl-4-heptylidine) amine/2,2-(di-2-methylpropyl)-4-ethyl-1,3-oxazolidine mixture (-×-), and the 2-(1-hydroxy-2-methylpropyl)(4-methyl-2-pentylidine) amine/2-(2-methylpropyl)-2,4,4-trimethyl-1,3-oxazolidine mixture (-◇-).

After the solution was prepared, samples of the solution were held at 25° C. and monitored by gas chromatography for the iminoalcohol, oxazolidine, amino alcohol and ketone and water content over a six hour period. The concentrations (moles/liter) of the above six materials were monitored as a function of time to determine if a particular iminoalcohol-oxazolidine mixture showed water scavenging activity. The relative water scavenging rates are illustrated in FIG. 3 which illustrates the water concentration as a function of time. The 2-(1-hydroxybutyl)(4-methyl-2-pentylidine) amine mixture, 2-(1-hydroxybutyl)(5-methyl-2-hexylidine) amine mixture and 2-(1-hydroxybutyl)(2-heptylidine) amine mixture were shown to be the most effective moisture scavengers.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims. Any $R_7$ group which can activate a ring opening, such as an ethyl group or an amine, aldimine or ketimine containing group, is preferred. Any R group substituents which increase the reactivity of a compound of the present invention to water or formaldehyde are within the scope of the present invention. For example, alkenyl and alkynl groups or substituent R groups may be selected as R group substituents if these groups increase the reactivity of the compound to water or formaldehyde. Likewise, any R group substituents which increase the reactivity of a reactive diluent compound to the active material whose concentration is to be reduced are within the scope of the present invention. Additionally, any R group substituents which improve the ability of a compound of the present invention to lower the freezing point of a preparation, provide improved solvency or pigment dispersability in a dispersion, suspension or solution, reduce the viscosity and improve the rheological properties of a preparation, or remove the color from a preparation are also preferred.

We claim:

1. A method of scavenging moisture from a preparation, wherein the method comprises admixing with the preparation from 1 mole to about 100 moles of a moisture scavenging compound for every mole of water to be dehydrated from the preparation, the moisture scavenging compound being selected from the group consisting of:

an iminoalcohol compound having the structure:

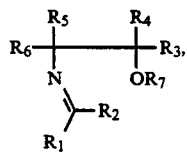

an oxazolidine compound having the structure:

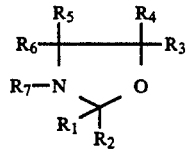

and a mixture of the iminoalcohol compound and the oxazolidine compound wherein: $R_1$ and $R_2$ are, individually, selected from the group consisting of a methyl or methyylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

2. The method of claim 1 including from 1 mole to about 10 moles of said moisture scavenging compound for every mole of water to be dehydrated in the preparation.

3. The method of claim 1 including from 1 mole to about 3 moles of said moisture scavenging compound for every mole of water to be dehydrated in the preparation.

4. The method of claim 1 wherein the preparation is selected from the group consisting of a composite, sacrificial pigment, gas, ink, industrial fluid, coating, adhesive, sealant, and coating component.

5. The method of claim 4 wherein the preparation is a composite, and further including the step of curing the composite after the moisture scavenging compound is admixed with the composite.

6. The method of claim 4 wherein the preparation is an ink, and the moisture scavenging compound is admixed with the ink after flushing of the ink.

7. The method of claim 4 wherein the preparation is a coating component selected from the group consisting of polyols, solvents, pigments, wetting agents, dispersants, flow additives, and fillers.

8. A method of inhibiting corrosion of a metal or alloy, wherein the method comprises contacting the metal or alloy with at least one mole of a corrosion inhibiting compound for every mole of water to be removed from a surface of the metal or alloy, the corrosion inhibiting compound being selected from the group consisting of:

an iminoalcohol compound having the structure:

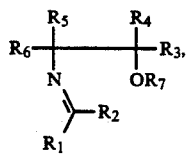

an oxazolidine compound having the structure:

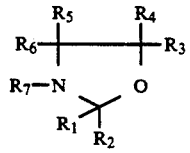

and a mixture of the iminoalcohol compound and the oxazolidine compound wherein: $R_1$ and $R_2$ are, individually, selected from the group consisting of a methyl or methylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

9. The method of claim 8 further including the step of coating the metal or alloy with the corrosion inhibiting compound.

10. The method of claim 8 wherein the corrosion inhibiting compound is admixed with an industrial fluid.

11. The method of claim 10 including from 1 mole to about 100 moles of said corrosion inhibiting compound for every mole of water to be removed from the industrial fluid.

12. The method of claim 10 including from 1 mole to about 10 moles of said corrosion inhibiting compound for every mole of water to be removed from the industrial fluid.

13. The method of claim 10 including from 1 mole to about 3 moles of said corrosion inhibiting compound for every mole of water to be removed from the industrial fluid.

14. A method of reducing foaming of a thermoplastic comprising admixing with the thermoplastic at least one mole of an antifoamant for every mole of water to be reacted in the thermoplastic, the antifoamant being selected from the group consisting of:

an iminoalcohol compound having the structure:

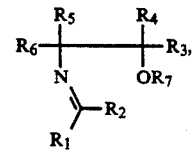

an oxazolidine compound having the structure:

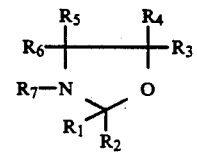

and a mixture of the iminoalcohol compound and the oxazolidine compound wherein: $R_1$ and $R_2$ are, individually, selected from the group consisting of a methyl or methylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

15. The method of claim 14 including from 1 mole to about 100 moles of said antifoamant for every mole of water to be reacted in the thermoplastic.

16. The method of claim 14 including from 1 mole to about 10 moles of said antifoamant for every mole of water to be reacted in the thermoplastic.

17. The method of claim 14 including from 1 mole to about 3 moles of said antifoamant for every mole of water to be reacted in the thermoplastic.

* * * * *